United States Patent
Egeblad et al.

(10) Patent No.: US 10,661,224 B2
(45) Date of Patent: May 26, 2020

(54) PROCESS FOR THE PURIFYING OF A RAW GAS STREAM CONTAINING MAINLY C1-C5 HYDROCARBONS AND CARBON DIOXIDE, AND IMPURITIES OF ORGANIC AND INORGANIC SULFUR COMPOUNDS, HALOGENATED AND NON-HALOGENATED VOLATILE ORGANIC COMPOUNDS AND OXYGEN

(71) Applicant: Haldor Topsøe A/S, Kgs. Lyngby (DK)

(72) Inventors: Kresten Egeblad, Farum (DK); Niklas Bengt Jakobsson, Kågeröd (SE); Jacob Hjerrild Zeuthen, Birkerød (DK); Rasmus Trane-Restrup, Roskilde (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/092,609

(22) PCT Filed: May 10, 2017

(86) PCT No.: PCT/EP2017/061134
§ 371 (c)(1),
(2) Date: Oct. 10, 2018

(87) PCT Pub. No.: WO2017/202608
PCT Pub. Date: Nov. 30, 2017

(65) Prior Publication Data
US 2019/0126199 A1 May 2, 2019

(30) Foreign Application Priority Data

May 24, 2016 (DK) .................................. 2016 00309
Oct. 17, 2016 (DK) .................................. 2016 00634
Jan. 12, 2017 (DK) .................................. 2017 00029

(51) Int. Cl.
| | | |
|---|---|---|
| *B01D 53/86* | (2006.01) | |
| *B01D 53/68* | (2006.01) | |
| *C10L 3/10* | (2006.01) | |
| *B01D 53/50* | (2006.01) | |
| *C12M 1/00* | (2006.01) | |
| *B01D 53/04* | (2006.01) | |
| *B01D 53/047* | (2006.01) | |
| *B01D 53/34* | (2006.01) | |
| *B01D 53/78* | (2006.01) | |

(52) U.S. Cl.
CPC ....... *B01D 53/8603* (2013.01); *B01D 53/047* (2013.01); *B01D 53/0462* (2013.01); *B01D 53/343* (2013.01); *B01D 53/50* (2013.01); *B01D 53/501* (2013.01); *B01D 53/68* (2013.01); *B01D 53/78* (2013.01); *B01D 53/869* (2013.01); *B01D 53/8662* (2013.01); *B01D 53/8668* (2013.01); *B01D 53/8671* (2013.01); *C10L 3/101* (2013.01); *C10L 3/103* (2013.01); *C10L 3/104* (2013.01); *C12M 47/18* (2013.01); *B01D 2251/202* (2013.01); *B01D 2251/21* (2013.01); *B01D 2251/304* (2013.01); *B01D 2251/404* (2013.01); *B01D 2251/604* (2013.01); *B01D 2251/606* (2013.01); *B01D 2257/104* (2013.01); *B01D 2257/204* (2013.01); *B01D 2257/206* (2013.01); *B01D 2257/30* (2013.01); *B01D 2257/302* (2013.01); *B01D 2257/306* (2013.01); *B01D 2257/504* (2013.01); *B01D 2257/553* (2013.01); *B01D 2257/556* (2013.01); *B01D 2257/708* (2013.01); *B01D 2258/05* (2013.01); *C10L 2200/0469* (2013.01); *C10L 2230/02* (2013.01); *C10L 2290/06* (2013.01); *C10L 2290/26* (2013.01); *C10L 2290/541* (2013.01); *C10L 2290/542* (2013.01); *C10L 2290/545* (2013.01)

(58) Field of Classification Search
None
See application file for complete search history.

(56) References Cited

U.S. PATENT DOCUMENTS

| | | | | |
|---|---|---|---|---|
| 3,760,061 | A * | 9/1973 | Hammond | B01D 53/507 423/243.01 |
| 5,292,704 | A * | 3/1994 | Lester | A62D 3/38 502/309 |
| 2003/0194366 | A1* | 10/2003 | Srinivas | B01D 53/8612 423/230 |
| 2007/0003477 | A1 | 1/2007 | Beraud et al. | |
| 2013/0095014 | A1 | 4/2013 | Grill | |
| 2013/0209338 | A1 | 8/2013 | Prasad et al. | |
| 2013/0340616 | A1* | 12/2013 | Iyer | C10L 3/08 95/186 |
| 2015/0119623 | A1 | 4/2015 | Huang | |

FOREIGN PATENT DOCUMENTS

| | | | | |
|---|---|---|---|---|
| CA | 1 326 342 | C | 1/1994 | |
| CN | 103159580 | A * | 6/2013 | |
| EP | 0 830 198 | B1 | 3/2002 | |
| EP | 1 997 549 | A1 | 12/2008 | |
| FR | 2 856 049 | A1 | 12/2004 | |
| GB | 2466554 | A * | 6/2010 | B01D 53/75 |
| WO | WO 96/39243 | A1 | 12/1996 | |
| WO | WO 2012/006729 | A1 | 1/2012 | |

OTHER PUBLICATIONS

CN-103159580-A English Translation (Year: 2013).*

* cited by examiner

*Primary Examiner* — Anita Nassiri-Motlagh
(74) *Attorney, Agent, or Firm* — Blank Rome LLP

(57) ABSTRACT

A method for the purification of a raw gas stream by selective catalytic oxidation, in which organic and inorganic sulfur compounds, halogenated and non-halogenated volatile organic compounds are selectively oxidized without substantially oxidizing the lower hydrocarbons and the sulfur containing compounds present in the gas to sulfur trioxide and excess of oxygen is removed by oxidation of lower alcohols, ethers or hydrogen added to the raw gas stream upstream the catalytic oxidation.

18 Claims, No Drawings

PROCESS FOR THE PURIFYING OF A RAW GAS STREAM CONTAINING MAINLY C1-C5 HYDROCARBONS AND CARBON DIOXIDE, AND IMPURITIES OF ORGANIC AND INORGANIC SULFUR COMPOUNDS, HALOGENATED AND NON-HALOGENATED VOLATILE ORGANIC COMPOUNDS AND OXYGEN

The present invention relates to a process for the purification of a raw gas stream containing lower hydrocarbons which is useful as fuel, as feed gas for downstream chemical reactions, or for injection into a natural gas pipeline, production of compressed methane gas for vehicle fuel or similar application after suitable separation and purification.

Typical raw gas streams are waste gas or product gas from sources including biogas streams. Those raw gas streams contain, beside desired lower hydrocarbons, impurities, the content of which must be removed or considerably reduced prior to employment of the raw gas stream for other uses. Biogas is a waste gas or product gas from sources including landfills and anaerobic digesters. In general, many raw gas streams contain an assortment of impurities, including organic and inorganic sulfur compounds, halogenated and non-halogenated volatile organic compounds.

Gas cleaning and purification is needed prior to employment of those raw gas streams. One of the reasons that raw gas streams must be cleaned prior to use is that sulfur and halogenated impurities can create a corrosive environment inside power generating equipment or even poison catalysts that may be present in any downstream application. Likewise, sulfur and halogenated impurities must typically be removed or substantially reduced to allow for a gas stream to be of a quality suitable for injection into a natural gas pipeline or similar application. Furthermore, hydrogen sulfide present in the feed gas to gas engines will cause degradation of the lubricating oil and lead to a need of frequent maintenance. Another reason to clean biogas is that other impurities, such as siloxanes, can be deposited within heat and power generation equipment and cause significant damage to the internal components.

Other reasons for raw gas cleaning and purification are that volatile organic compounds (VOC) are not desired when raw gas is used alone or in combination with methane or natural gas as renewable form of energy in pipeline quality or as feed gas for the preparation of chemicals.

Additionally, in many applications, oxygen is not desired in a purified raw gas when employed in combination with methane or natural gas as renewable form of energy in pipeline quality or as feed gas for the preparation of chemicals.

By use of known separation and purification technology, such as pressure and/or temperature swing adsorption (PSA/TSA), amine scrubbing, membranes, solid and liquid regenerative or non-regenerative scavengers, etc. it is difficult, cumbersome and costly to separate and purify lower hydrocarbons, in particular methane, from such a mixture to meet the specified composition or natural gas pipeline limits.

The major problem concerned with the above technologies to remove sulfur containing compounds and halogenated compounds from waste gas streams, especially biogas streams from landfills and anaerobic digesters, is that they add up to significant capital costs as well as operational costs. They also add significantly to the operation and equipment complexity for these relatively small treatment units.

As an example, a typical purification train required for upgrading a typical raw gas stream to be of a quality suitable for injection into a natural gas pipeline or similar application is to first subject the raw gas to an amine wash unit, which facilitates separation of the $CO_2$, $H_2S$ and partly other hydrophilic components from the lower hydrocarbons, $N_2$, $O_2$ and most other hydrophobic components. The lower hydrocarbon bearing stream needs subsequent multiple purification steps to remove VOCs, halogenated organic compounds, and optionally present $N_2$, $O_2$, water and siloxanes, when present.

We found that subjecting a raw gas stream to a catalytic oxidation, in which organic and inorganic sulfur compounds, halogenated and non-halogenated volatile organic compounds are selectively oxidized without substantially oxidizing the lower hydrocarbons and the sulfur containing compounds present in the gas to sulfur trioxide, results in a significantly simpler and less costly separation and purification to meet feed gas or pipeline requirements.

In a number of applications, oxygen is not desired in the purified raw gas when employed in combination with methane or natural gas as renewable form of energy in pipeline quality or as feed gas for the preparation of chemicals.

Additionally, we found that injection of easy oxidizable compounds into the raw gas stream prior to the catalytic oxidation allows for effective removal of excess of oxygen, not having been consumed in the oxidation of the sulfur and volatile organic compounds.

Because of their higher reduction potential compared to hydrocarbons, lower alcohols, including methanol, ethanol and propanol or mixtures thereof, and corresponding lower ethers and hydrogen are the preferred reductants in the method according to the invention.

The reductant is added to the gas upstream to one or more oxidation steps or between a first oxidation step and a second oxidation step.

Pursuant to this finding, this invention provides a process for purifying of a raw gas containing mainly C1-C5 hydrocarbons and carbon dioxide, and impurities of organic and inorganic sulfur compounds, halogenated and non-halogenated volatile organic compounds, oxygen, nitrogen and water, without substantially oxidizing the C1-C5 hydrocarbons and without substantially oxidizing the organic and inorganic sulfur compounds to sulfur trioxide, the process comprises the steps of contacting the raw gas at a temperature of between 200 and 450° C. in one or more oxidation steps with a selective oxidation catalyst and oxidizing selectively in part or in full the organic and inorganic sulfur compounds and the halogenated and non-halogenated volatile organic compounds to carbon dioxide, water, sulfur dioxide and hydrogen halides; and removing at least part of excess of oxygen contained in the raw gas in the one or more oxidation steps by adding lower alcohols, lower ethers, hydrogen or combinations thereof to the raw gas upstream to at least one of the one or more oxidation steps and oxidizing the lower alcohols, lower ethers or hydrogen or combinations thereof to carbon dioxide and water with the at least part of the excess of oxygen;

withdrawing and cooling a hot exit gas from the one or more oxidation steps comprising the C1-C5 hydrocarbons, sulfur dioxide, carbon dioxide, water, hydrogen halides and being essentially free of oxygen; and introducing the cooled exit gas into a purification step and removing the sulfur dioxide and the hydrogen halides, from the cooled exit gas; and collecting a purified exit gas comprising the C1-C5 hydrocarbons, carbon dioxide and water.

In applications where the raw gas stream feed to the oxidation step(s) contains high amounts of oxygen resulting in an undesired temperature increase due to the exothermic oxidation reaction of the lower alcohols, lower ethers and/or hydrogen, it is advantageous to perform a first oxidation step without or limited, e.g. understoichiometric addition of the lower alcohols, lower ethers and/or hydrogen and removing excess of oxygen in the exit gas from the first oxidation step not having been used in the first oxidation step in a subsequent second oxidation step.

Thus, in an embodiment of the invention, the one or more oxidation steps comprise a second oxidation step arranged subsequently to a first oxidation step for the removal of remaining excess of oxygen contained in the raw gas from the first oxidation step by adding lower alcohols, lower ethers, hydrogen or combinations thereof to the raw gas withdrawn from the first oxidation step and oxidizing the lower alcohols or lower ethers or hydrogen or combinations thereof to carbon dioxide and water and the hot exit gas is withdrawn from the second oxidation step.

In the above embodiment it is preferred to cool the raw gas from the first oxidation step prior to the second oxidation step, preferably by heat exchange with the raw gas being passed to the first oxidation step.

Alternatively, the more oxidations steps can be carried out in parallel, by dividing the raw gas stream in two or more substreams and passing the substreams after addition of the lower alcohols and/or lower ethers and/or hydrogen to one or more of the oxidation steps.

A preferred selective oxidation catalyst for use in the invention comprises oxides of vanadium, tungsten and titanium and metallic or oxidic platinum and/or palladium.

Preferably, the selective oxidation catalyst is supported on a monolithic substrate.

As mentioned hereinbefore many raw gas streams may further contain harmful siloxanes and silanols.

Thus, the purification method according to a specific embodiment of the invention comprises the additional step of removing siloxanes and silanols optionally further contained in the raw gas stream by passing the raw gas stream through a siloxane removal device, preferably a siloxane absorption bed, prior to the one or more oxidation steps.

The additional step of removing siloxanes is preferably carried out by heating the raw gas stream and passing the heated raw gas stream through a siloxane absorption bed prior to the oxidation step(s).

It is known that siloxanes can be removed using non-regenerative packed bed adsorption with activated carbon, porous silica or alumina as sorbent. Regenerative sorbents can also be used as well as units based on gas cooling to very low temperatures to precipitate the siloxanes out from the gas. Further, liquid extraction technologies are used. In addition, these technologies can be used in combination.

Regenerative systems using activated alumina, activated alumina plus silica and activated carbon adsorbents to capture siloxanes and silanols have been reported. After saturation of the adsorbent with siloxane impurities, the adsorbed siloxanes are removed in situ using pressure swing adsorption (PSA) or thermal swing adsorption (TSA) to enable the bed to be re-used.

In the method of the invention sulfur compounds and halogenated organic compounds are catalytically oxidized to carbon dioxide, water, sulfur dioxide and hydrogen halides.

The sulfur dioxide and hydrogen halides are then in a specific embodiment of the invention removed in the purification step by scrubbing the cooled exit gas using a caustic scrubber agent.

Preferred scrubbing agents comprise an aqueous solution of NaOH, $Ca(OH)_2$ or $CaCO_3$.

Optionally, it might be preferable to oxidize sulfur dioxide contained in the cooled exit gas to sulfuric acid.

In this case, sulfur dioxide and hydrogen halides are removed from the cooled exit gas in the purification step by scrubbing the cooled exit gas in a scrubber using hydrogen peroxide to produce sulfuric acid.

Carbon dioxide also contained in the purified raw gas stream is preferably removed by pressure or temperature swing adsorption or chemical or physical carbon dioxide absorption, known in the art.

All embodiments of the invention are specifically useful in the removal or substantially reduction of halogenated volatile organic compounds comprising halogenated aliphatic and/or aromatic organic compounds, including but not limited to mono-, di-, or tri-chloro ethane, mono- or di-chloro benzene, vinyl chloride, and dioxins.

The method according to the invention is also effective in the removal or reduction of fully substituted chloro-fluoro compounds and tetra-chloro ethylene Furthermore, the invention is effective in the removal or reduction of contents of non-halogenated volatile organic compounds comprising acyclic and/or cyclic alkanes, alkenes and/or alkynes, non-alkylated, alkylated or alkenylated aromatic compounds, and/or oxygenated compounds, such as for example hexane, heptane, cyclohexane, limonene, benzene, toluene, ethyl benzene, xylenes, styrene, acetone, ethyl acetate, and isopropyl alcohol.

All embodiments of the inventions are useful for the purification of a raw gas stream of biogas from landfills or anaerobic digesters.

The invention claimed is:

1. A process for purifying of a raw gas containing C1-C5 hydrocarbons and carbon dioxide, and impurities of organic and inorganic sulfur compounds, halogenated and non-halogenated volatile organic compounds, oxygen, nitrogen and water, without oxidizing the C1-C5 hydrocarbons and without oxidizing the organic and inorganic sulfur compounds to sulfur trioxide, the process comprises the steps of contacting the raw gas at a temperature of between 200 and 450° C. in one or more oxidation steps with a selective oxidation catalyst and oxidizing selectively in part or in full the organic and inorganic sulfur compounds and the halogenated and non-halogenated volatile organic compounds to carbon dioxide, water, sulfur dioxide and hydrogen halides; and removing at least part of excess of oxygen contained in the raw gas in the one or more oxidation steps by adding lower alcohols, lower ethers, or combinations thereof to the raw gas upstream to at least one of the one or more oxidation steps and oxidizing the lower alcohols, lower ethers or combinations thereof to carbon dioxide and water with the at least part of the excess of oxygen;

withdrawing and cooling a hot exit gas from the one or more oxidation steps comprising the C1-C5 hydrocarbons, sulfur dioxide, carbon dioxide, water, and hydrogen halides, with at least part of the excess of oxygen removed from the exit gas; and introducing the cooled exit gas into a purification step and removing the sulfur dioxide and the hydrogen halides, from the cooled exit gas; and collecting a purified exit gas comprising the C1-C5 hydrocarbons, carbon dioxide and water.

2. Process according to claim 1, wherein the one or more oxidation steps comprise a second oxidation step arranged subsequently to a first oxidation step for the removal of remaining excess of oxygen contained in the raw gas from the first oxidation step by adding lower alcohols, lower ethers, or combinations thereof to the raw gas withdrawn from the first oxidation step and oxidizing the lower alcohols or lower ethers or combinations thereof to carbon dioxide and water and the hot exit gas is withdrawn from the second oxidation step.

3. Process according to claim 2, wherein the raw gas from the first oxidation step is cooled prior to the second oxidation step.

4. Process according to claim 3, wherein the raw gas is cooled by heat exchange with the raw gas being passed to the first oxidation step.

5. Process according to claim 1, wherein the one or more oxidation steps are performed in parallel.

6. Process according to claim 1, wherein the selective oxidation catalyst in the one or more oxidation steps comprises oxides of vanadium, tungsten, and titanium, with metallic or oxidic palladium.

7. Process according to claim 1, comprising an additional step of removing siloxanes and silanols contained in the raw gas stream by passing the raw gas stream through a siloxane and silanol sorbent, prior to the one or more oxidation steps.

8. Process according to claim 7, wherein the additional step of removing siloxanes and silanols contained in the raw gas stream is carried out by heating the raw gas stream prior to passage through the siloxane and silanol sorbent.

9. Process according to claim 1, wherein the sulfur dioxide and hydrogen halides are removed from the cooled exit gas by scrubbing the cooled exit gas using a caustic scrubbing agent.

10. Process according to claim 9, wherein the caustic scrubbing agent comprises an aqueous solution of NaOH, $Ca(OH)_2$ or $CaCO_3$.

11. Process according to claim 1, wherein sulfur dioxide and hydrogen halides are removed by scrubbing the cooled exit gas in a scrubber using hydrogen peroxide to produce sulfuric acid.

12. Process according to claim 1, wherein carbon dioxide contained in the purified raw gas stream is removed by pressure or temperature swing absorption or chemical or physical carbon dioxide absorption.

13. Process according to claim 1, wherein the selective oxidation catalyst is supported on a monolithic substrate.

14. Process according to claim 1, wherein the halogenated volatile organic compounds comprise halogenated aliphatic and/or aromatic organic compounds.

15. Process according to claim 1, wherein the raw gas stream contains fully substituted chloro-fluoro compounds and tetra-chloro ethylene.

16. Process according to claim 1, wherein the non-halogenated volatile organic compounds comprise acyclic and/or cyclic alkanes, alkenes and/or alkynes, non-alkylated, alkylated or alkenylated aromatic compounds, and/or oxygenated compounds.

17. Process according to claim 1, wherein the raw gas stream is a biogas stream from landfills or anaerobic digesters.

18. Process according to claim 14, wherein the halogenated volatile organic compounds comprise mono-, di-, or tri-chloro ethane, mono- or di-chloro benzene, vinyl chloride, or dioxins.

* * * * *